(12) United States Patent
Igarashi

(10) Patent No.: US 6,471,642 B1
(45) Date of Patent: Oct. 29, 2002

(54) RIGID ENDOSCOPE OPTICAL SYSTEM

(75) Inventor: Tsutomu Igarashi, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 195 days.

(21) Appl. No.: 09/680,301

(22) Filed: Oct. 6, 2000

(30) Foreign Application Priority Data

Oct. 8, 1999 (JP) ............................................ 11-288135

(51) Int. Cl.7 ................................................. A61B 1/06
(52) U.S. Cl. ...................... 600/166; 600/111; 600/175; 348/65; 359/362
(58) Field of Search ................................. 600/166, 160, 600/111, 109, 175, 167; 348/65, 67; 359/362, 660, 435, 708

(56) References Cited

U.S. PATENT DOCUMENTS

| | | | |
|---|---|---|---|
| 4,916,534 A | * 4/1990 | Takahashi et al. | ........... 600/175 |
| 5,083,223 A | * 1/1992 | Igarashi | ...................... 359/708 |
| 5,087,989 A | * 2/1992 | Igarashi | ...................... 359/708 |
| 5,177,605 A | * 1/1993 | Takahashi et al. | ............. 348/65 |
| 5,198,931 A | * 3/1993 | Igarashi | ...................... 359/660 |
| 5,743,846 A | 4/1998 | Takahashi et al. | |
| 5,852,511 A | * 12/1998 | Tateyama et al. | ........... 359/362 |
| 5,933,275 A | * 8/1999 | Igarashi | ...................... 359/435 |
| 5,971,915 A | 10/1999 | Yamamoto et al. | |
| 6,163,401 A | * 12/2000 | Igarashi | ...................... 359/435 |

FOREIGN PATENT DOCUMENTS

| | | |
|---|---|---|
| JP | 7-261099 | 10/1995 |
| JP | 8-122665 | 5/1996 |
| JP | 11-6967 | 1/1999 |

* cited by examiner

Primary Examiner—Teresa Walberg
Assistant Examiner—Fadi H. Dahbour
(74) Attorney, Agent, or Firm—Armstrong, Westerman & Hattori, LLP

(57) ABSTRACT

A rigid endoscope optical system which can obtain both a wide angle image for finding an organ and a high resolution image used for a precise treatment. The rigid endoscope optical system has objective optical systems for stereoscopic observation which forms right and left images. The rigid endoscope optical system also has a secondary objective optical system which has a field of view different from the objective optical system for stereoscopic observation, and one relay optical system which transmits the images of the objective optical system for stereoscopic observation and the secondary objective optical system.

14 Claims, 4 Drawing Sheets

RIGID ENDOSCOPE OPTICAL SYSTEM

BACKGROUND OF THE INVENTION

This invention relates to a rigid endoscope optical system, especially to a stereoscopic rigid endoscope system.

Conventionally, the stereoscopic endoscope is known as described in, for example, Japanese Laid-Open Publication No. 7-261099, Japanese Laid-Open Publication No. 8-122665, and Japanese Laid-Open Publication No. 11-6967.

In endoscopic surgery, both wide angle and magnified images are required. The wide angle image is used for finding an organ, a disease, or a treatment tool, while the magnified image is used for treatment. A conventional rigid endoscope usually has only one observation optical system. When a wide angle objective lens is arranged in the optical system, above-mentioned need is carried out by using one of following methods.

(A) Changing distance to the object
(B) Using optical zoom function on the side of TV camera system connected to the optical System On the one hand, endoscopic robot surgery system has been developed recently. In this case, surgical treatment tools and an endoscope are operated remotely by a surgeon. Since such robot enables precise surgical treatment, surgeons require endoscopes to have better images with higher magnification and higher resolution at the time of treatment.

When either of the above methods (A) or (B) are used in endoscopic robot surgery in order to magnify the image of a object, some problems arise.

In method (A), if a rigid endoscope is brought close to a target object, interference between the endoscope and treatment tools will pose a problem. Therefore, the field angle of view should be narrow at the time of a treatment to get both high magnification and long working distance(WD). However, if an objective lens is made into a narrow angle, the wide angle image for finding will not be obtained.

In method (B), a combination of a wide angle rigid endoscope and a camera system with optical zoom function enables both wide image and high magnification image. But the high magnification image has worse image quality than the wide image because the point spread property of a rigid endoscope is fixed and the final point spread property at the imaging surface in the camera system is magnified according to the optical zoom state in the camera system. That is, the longer focal length of the zoom optics makes the final point spread property worse. This deterioration of image quality in a high magnification state cannot be tolerated for precise treatment.

Moreover, in the endoscopic robot surgery system, a stereoscopic rigid endoscope system is preferred in order to obtain a depth perception. In this case, however, there are the following problems in addition to the above problems.

First, it is more difficult to get good image quality than in the case of a two-dimensional image (2D). In the stereo endoscope, it is necessary to transmit the right and left images within the space of the limited insertion part. In this case, the image quality of the stereo endoscope will be degraded more than in the case of 2D.

Second it is difficult to add a zoom function in the stereo endoscope system, while keeping the right and left optical conditions satisfied.

SUMMARY OF THE INVENTION

In view of the foregoing disadvantages inherent in the known types of prior art, the present invention solves the above-mentioned problems. Thus, it is an object of the present invention to provide a rigid endoscope optical system which enables both the wide angle image for finding an organ or treatment tools and the high resolution image used for a precise treatment. In addition, to provide the suitable optical system for a stereo endoscope system.

The first rigid endoscope optical system of this invention which attains the above objectives comprises a primary objective optical system, a secondary objective optical system with a wider field of view than the primary objective optical system, and a relay optical system which transmits images or pupils made by these objective optical systems.

As constructed as described above, it is possible to obtain both a wide angle image used for finding and a narrow angle image with high resolution used for the precise treatment. Since the present invention uses a common relay optical system, and the relay optical system has a larger outer diameter, the relay optical system has lower optical performance requirements and fewer manufacturing errors than the case of using respective relay optical systems which correspond to the primary and the secondary objective optical systems. Therefore, the image quality deterioration after assembling is small. Moreover, the number of lenses in the relay optical system is reduced and the larger outer diameter of lenses increases manufacturing workability. Therefore, the present invention decreases the total cost of the relay optical system.

It is desirable that both the primary and secondary objective optical systems have nearly the same direction of view regardless of direct or oblique direction of view.

In the case of getting an oblique direction of view, it is desirable that both the primary and the secondary objective optical systems share a prism unit to get an oblique field direction. In the case of using respective prism units corresponding to the primary and secondary objective optical systems, it is difficult to reduce differences in direction of view between the primary and the secondary objective optical systems without precise adjustment. However, if the prism unit is made to share, the difference in direction of view will be made small without adjustments.

The present invention has two methods of transferring images made by the primary and the secondary objective optical systems. The first transfer method is to make real images just before the relay optical system and the second transfer method is to make pupils just before the relay optical system. In the first transfer method, the primary and the secondary objective optical systems are terminated by the real images and the relay optical system transmits the images to the final image plane of the relay optical systems. In this case, it is desirable that the primary and the secondary objective optical systems make real images on a nearly identical image plane and the images do not overlap on the image plane. If the images overlap on the image plane, it is impossible to separate the images completely after the relay optical system without partial lack of images. Accordingly, it is desirable to take such an arrangement.

In this case, it is desirable to have an optical means on the rear side of the relay optical system to separate the real images made by the relay optical system.

In the second transfer method, the primary and the secondary objective optical systems are terminated by the exit pupils and the relay optical system transmits the pupils to the exit pupil plane of the relay optical systems. In this case, it is desirable that the primary and the secondary objective optical systems make exit pupils on a nearly identical pupil plane and the pupils do not overlap on the pupil plane. The plane of the exit pupils made by the objective optical systems becomes an entrance pupil plane of the relay system. If the pupils overlap on the pupil plane, it is impossible to separate the pupils completely after the relay optical system without cross-talk (the image of a certain objective optical system mixes with the image of the other objective optical system). Accordingly, it is desirable to take such an arrangement.

In this case, it is desirable to have an optical means on the rear side of the relay optical system to separate the pupils made by the relay optical system.

In addition, it is desirable that the primary and the secondary objective optical systems form intermediate real images in their respective objective optical systems. If there were no optical systems for forming the intermediate real images, aberrations of each optical systems should be independently minimized. Therefore, the primary and the secondary objective optical systems and the relay optical system need to be independently optimized, respectively. If each objective optical system has no intermediate real images, it is difficult to correct aberrations and to get high quality images because of the few design variables in the lens constitution. Therefore, it is desirable that the primary and the secondary objective optical systems have intermediate real images, respectively.

Moreover, it is desirable that the primary objective optical system has a larger lens diameter than the secondary objective optical system. The primary objective optical system for treatment should be designed with high resolution. It is necessary for the primary objective optical system to have a large numerical aperture in order to get high resolution. Enlarging the lens diameter is one of the methods to get a large numerical aperture. Since the secondary objective optical system is used for finding, image quality of the secondary objective optical system is permissible even if it is somewhat bad.

Hereafter, the second rigid endoscope optical system of the present invention is explained. The second rigid endoscope optical system of the present invention comprises a primary objective optical system for stereoscopic observation which forms right and left images, a secondary objective optical system with wider field of view than the primary objective optical system for stereoscopic observation, and one relay optical system which transmits the images of these objective optical systems.

The primary objective optical system for stereoscopic observation is made to be able to get right and left images for stereoscopic observation. The secondary objective optical system is used for finding as in the first rigid endoscope optical system. All images made by the objective optical systems are transmitted by the relay optical system. Also in this case, the relay optical system has lower sensitivity against manufacturing error than the case of using respective relay optical systems which correspond to the primary and the secondary objective optical systems. Therefore, the image quality deterioration after assembling is small and total cost of the relay optical system is reduced as in the first rigid endoscope.

In this case, it is desirable that both the primary objective optical system for stereoscopic observation and the secondary objective optical system have nearly same direction of view regardless of direct or oblique direction of view. Especially in the stereoscopic observation, the direction of view of right and left images must be the same.

In the case of getting an oblique direction of view, it is desirable that both the primary stereoscopic and the secondary objective optical systems share a prism unit to get an oblique field direction. In the case of using respective prism units corresponding to the primary and secondary objective optical systems, it is difficult to reduce differences of the direction of view between the primary and the secondary objective optical systems without precise adjustment. However, if the prism unit is made to share, the difference in direction of view will be made small without adjusting. Especially since it is fatal if there a difference in direction of view between the right and left images, the shared prism is effective.

Moreover, the primary objective optical system for stereoscopic observation may have a right objective optical system and a left objective optical system independent of each other. Also both the first and the second image transfer methods are applicable in this embodiment. In the first transfer method, the right objective optical system, the left objective optical system, and the secondary objective optical system are terminated by the real images, and the relay optical system transmits the images to the final image plane of the relay optical systems. In this case, it is desirable that the left, the right, and the secondary objective optical systems make real images on a nearly identical image plane and the images do not overlap on the image plane. If the images overlap on the image plane, it is impossible to separate the images completely after the relay optical system without partial lack of images. Accordingly, it is desirable to take such an arrangement.

Also in this case, it is desirable to have an optical means on the rear side of the relay optical system to separate the real images made by the relay optical system.

In the second transfer method, the right, the left, and the secondary objective optical systems are terminated by the exit pupils and the relay optical system transmits the pupils to the exit pupil plane of the relay optical systems. In this case, it is desirable that the right, the left, and the secondary objective optical systems make exit pupils on a nearly identical pupil plane and the pupils do not overlap on the pupil plane. The plane of the exit pupils made by the objective optical systems becomes an entrance pupil plane of the relay system. If the pupils overlap on the pupil plane, it is impossible to separate the pupils completely after the relay optical system without cross-talk. Especially the cross-talk between the right and the left image is fatal for stereoscopic observation because the right image mixes the left image. Accordingly, it is desirable to take such arrangement.

Also in this case, it is desirable to have an optical means on the rear side of the relay optical system to separate the pupils made by the relay optical system.

In addition, it is desirable that the right, the left, and the secondary objective optical systems form intermediate real images in the respective objective optical systems for the same reasons as in the first rigid endoscope optical system.

Moreover, it is desirable that the left and the right objective optical system have larger lens diameter than the secondary objective optical system for the same reasons as in the first rigid endoscope optical system.

BRIEF EXPLANATION OF DRAWINGS

FIG. 2(*b*) illustrates a frontal plane view of pupil plane E2 and prisms PL and PR of the optical system of FIG. 1.

DETAILED DESCRIPTION OF THE PREFERRED EMBODIMENTS

Hereafter, the rigid endoscope optical system of this invention is explained based on embodiments which are designed to be able to have stereoscopic vision.

Figure 1:
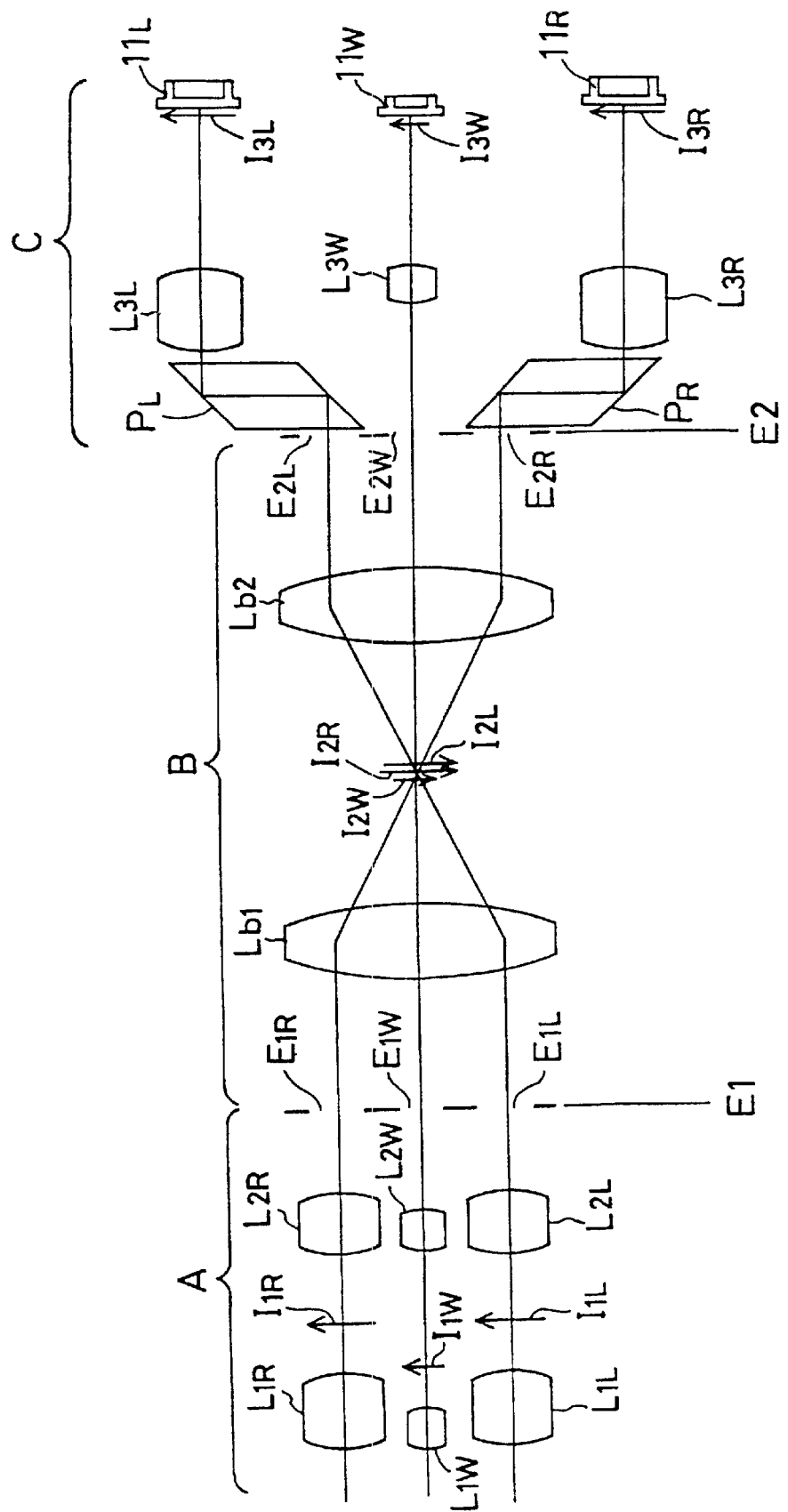
FIG. 1 is an optical-path diagram showing an stereoscopic rigid endoscope optical system according to the first embodiment of the present invention.

FIG. 1 is an optical-path diagram showing a stereoscopic rigid endoscope optical system according to the first embodiment. The stereoscopic rigid endoscope optical system comprises objective optical system part A, relay optical system part B, and image-formation optical system part C.

The objective optical system part A is equipped with the primary objective optical system for stereoscopic observation and the secondary objective lens system. The primary objective optical system for stereoscopic observation consists of L1L–L2L and L1R–L2R. The secondary objective optical system consists of L1W–L2W. L1L, L1R, and L1W are image-formation lens systems. L2L, L2R, and L2W are afocal conversion lens systems.

The lens systems L1L–L2L and L1R–L2R have the same optical property and comparatively narrow field of view. The secondary objective lens system L1W–L2W has a wider field of view than the primary objective optical system for stereoscopic observation.

Figure 2:
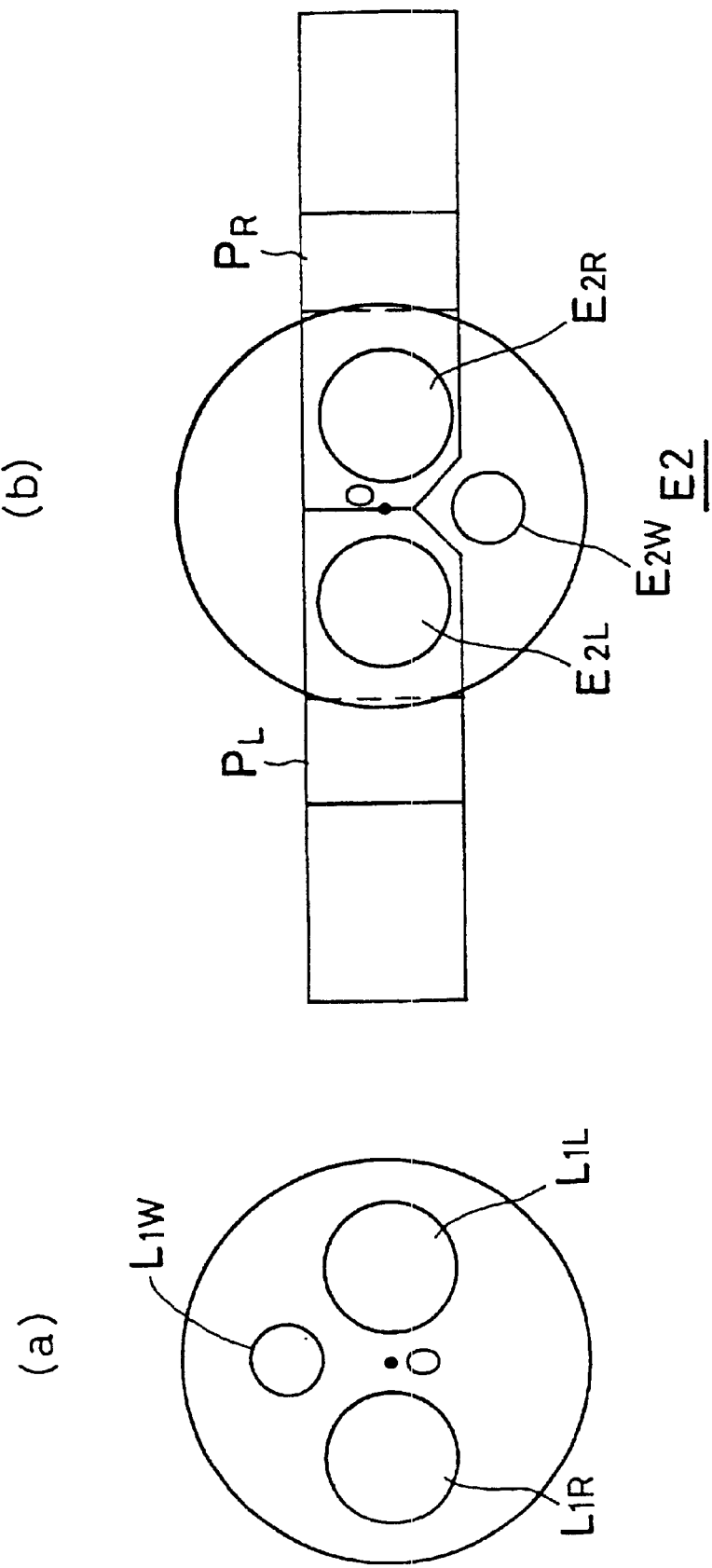
FIG. 2(*a*) illustrates a frontal plane view of part A of the optical system of FIG. 1.

FIG. 2(a) illustrates a frontal view of part A of the optical system of FIG. 1. The lens systems, L1L, L1R, and L1W, have certain angles around the central axis O as shown in FIG. 2(a), and are arranged so that they may have an parallel optical axis. However, FIG. 1 illustrates these three objective lens systems L1L–L2L, L1R–L2R, and L1W–L2W on the same plane in order to make explanation easy.

As for the lens systems L1L–L2L and L1R–L2R for stereoscopic observation, it is desirable to arrange them at positions with identical distances from the central axis O. The lens systems L1L and L1R used for stereoscopic observation have narrow fields of view and form images with high resolution. The lens system L1W has a wide field of view and is used for finding an organ.

For this reason, as shown in FIG. 2(a), the aperture diameter of the primary objective lens system L1L–L2L and L1R–L2R for stereoscopic observation is comparatively large. On the one hand, the aperture diameter of secondary objective lens system L1W–L2W is smaller than L1L–L2L and L1R–L2R.

At the rear side of L1L and L1R, the right and left afocal conversion lens system of the same optical property L2L and L2R are arranged. The images I1L and I1R made by L1L and L1R are transferred to the nearly infinite point by the lens systems L2L and L2R. Then, objective optical system exit pupil E1L and E1R on either side are formed apart on the same exit pupil plane E1.

Moreover, the lens system L2W is arranged on the same axis at the rear side of lens system L1W. The image I1W made by the lens system L1W is transferred to the nearly infinite point by the lens system L2W. Then, secondary objective optical system exit pupil E1W is formed apart from the objective optical system exit pupil E1L and E1R, on the same exit pupil plane E1.

These three objective optical systems are arranged in parallel and are designed so that their exit pupils may not be overlapped on the same exit pupil plane E1.

In the relay optical system part B, a pair of lens systems Lb1 and Lb2 are arranged. The exit pupil plane E1 of the objective optical system part A exists at the front focal plane of the first lens system Lb1. The pupil plane E1 becomes an entrance pupil plane of the relay optical system part B. The second pupil plane E2 which conjugates to the exit pupil plane E1 is formed at the rear focal plane of the 2nd lens system Lb2. And the front focal plane of Lb2 is arranged at the rear focal plane of Lb1.

On the second pupil plane E2, the objective optical system exit pupils E1L and E1R respectively conjugate the second exit pupils E2L and E2R. And the exit pupil E2W which conjugates to the secondary objective optical system exit pupil E1W is formed similarly apart. Moreover, three relay images I2L, I2R, and I2W are formed in piles on the rear focal plane of the lens system Lb1.

The relay optical system part B consists of only a cycle of lens system Lb1 and Lb2 in FIG. 1. However, the relay optical system part B may consist of two or more cycles of the lens system Lb1 and Lb2 to make the insertion length longer.

Image-formation optical system part C branches ray bundles passing through the pupils E2L, E2R, and E2W. In addition, the optical system part C forms final images I3L, I3R, and I3W on the image-pick-up elements (for example, CCD) 11L, 11R and 11W on either side with image-formation lens systems L3L, L3R and L3W.

The parallelogram prisms PL and PR may respectively be arranged near the pupils E2L and E2R on either side. PL is arranged to transfer only the ray bundle from the pupil E2L and PR is arranged to transfer only the ray bundle from the pupil E2R. The parallelogram prisms PL and PR shift optical axes respectively in the outside direction in parallel. And the final images I3L and I3R are formed respectively on image-pick-up element 11L and 11R by the right and left image-formation lens systems L3L and L3R of the same optical property.

In this embodiment, the optical path to get the wide angle image I3W is not shifted. And the wide angle image I3W is formed on the image-pick-up element 11W by the image-formation lens system L3W.

FIG. 2(b) is a frontal plane view of pupil plane E2 of FIG. 1. The prisms PL and PR of FIG. 2(b) are partially chipped so that the ray bundle from the pupil E2W may not be rejected by the prisms.

In FIG. 1, the lens systems L1L and L1R for stereoscopic observation and the secondary objective lens system L1W have the same direction of view. However, a common direction conversion optical means may be arranged in the front side of those objective lens systems L1L, L1R, and L1W to get oblique direction of view. The case where a conversion prism unit 12 common to the three lens systems L1L, L1R and L1W is shown in FIGS. 3(a), 3(b) and 3(c). FIG. 3(a) illustrates a side view, FIG. 3(b) a plan view, and FIG. 3(c) a perspective diagram.

The direction conversion prism unit 12 consists of two prism components which are cemented and includes incidence plane 15, reflecting plane 14, reflecting plane 13, and emission plane 16. The plane 14 is parallel to the axis of rear side of the objective optical system and is designed to have total-reflection property. The plane 13 is inclined to the axis and is designed to have total-reflection property. A ray injected from object side passes through the incidence plane 15, and is reflected by plane 14 and plane 13, and passes through the emission plane 16. All rays passing through the prism unit 12 are bent to the same direction by the prism unit 12. Therefore, the same oblique directions of view are obtained simultaneously using the prism unit 12 in common.

Figure 3:
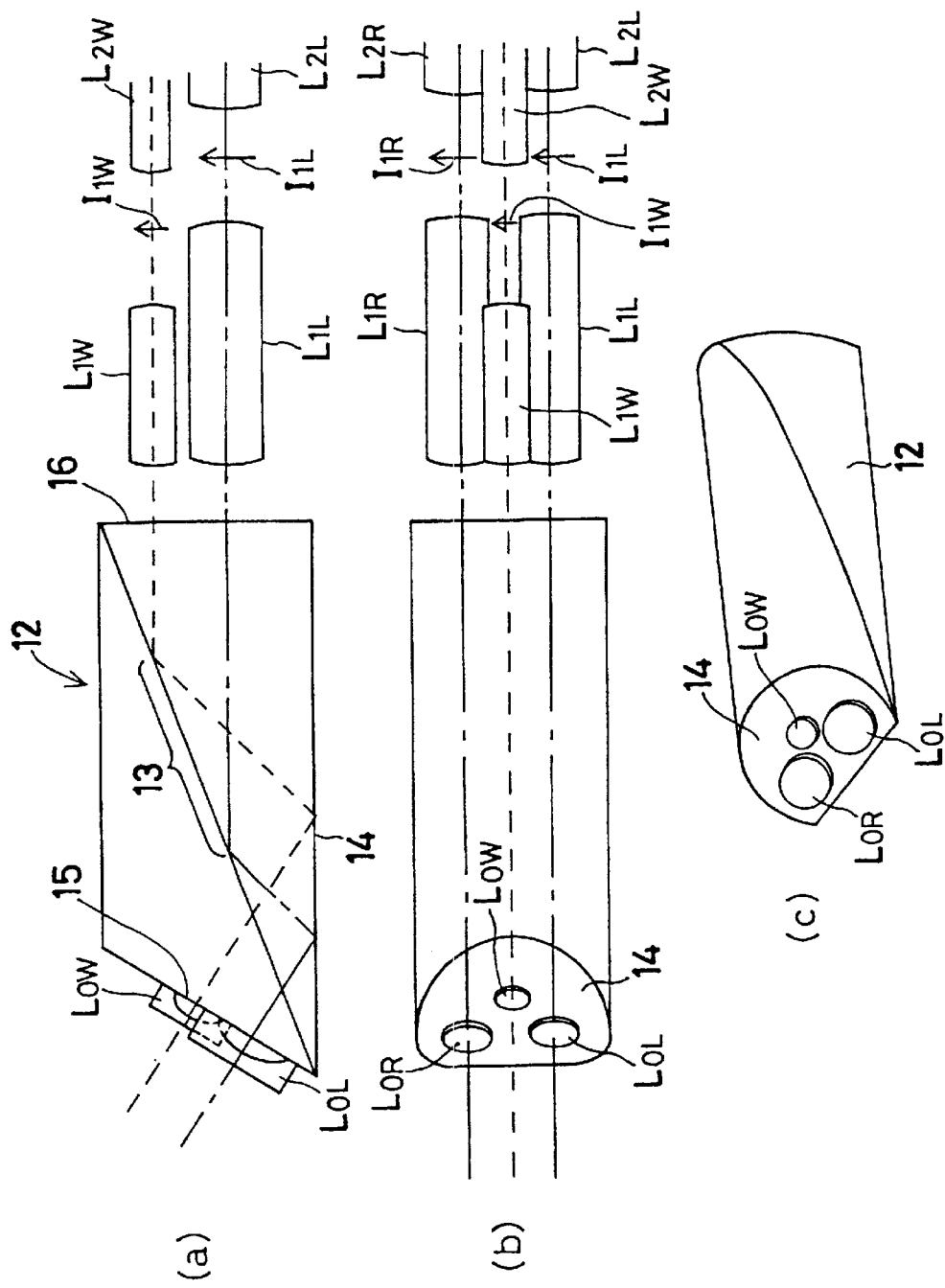
FIGS. 3(a)–3(c) illustrate a direction conversion prism unit used to get an oblique direction of view.

In addition, negative lenses L0L, L0R and L0W are arranged coaxially to the optical axes of L1L, L1R, and L1W on the incidence plane 15 of the prism unit 12 in FIG. 3. These lenses L0L, L0R, and L0W are the respective partial component of the lens systems L1L, L1R and L1W.

Figure 4:
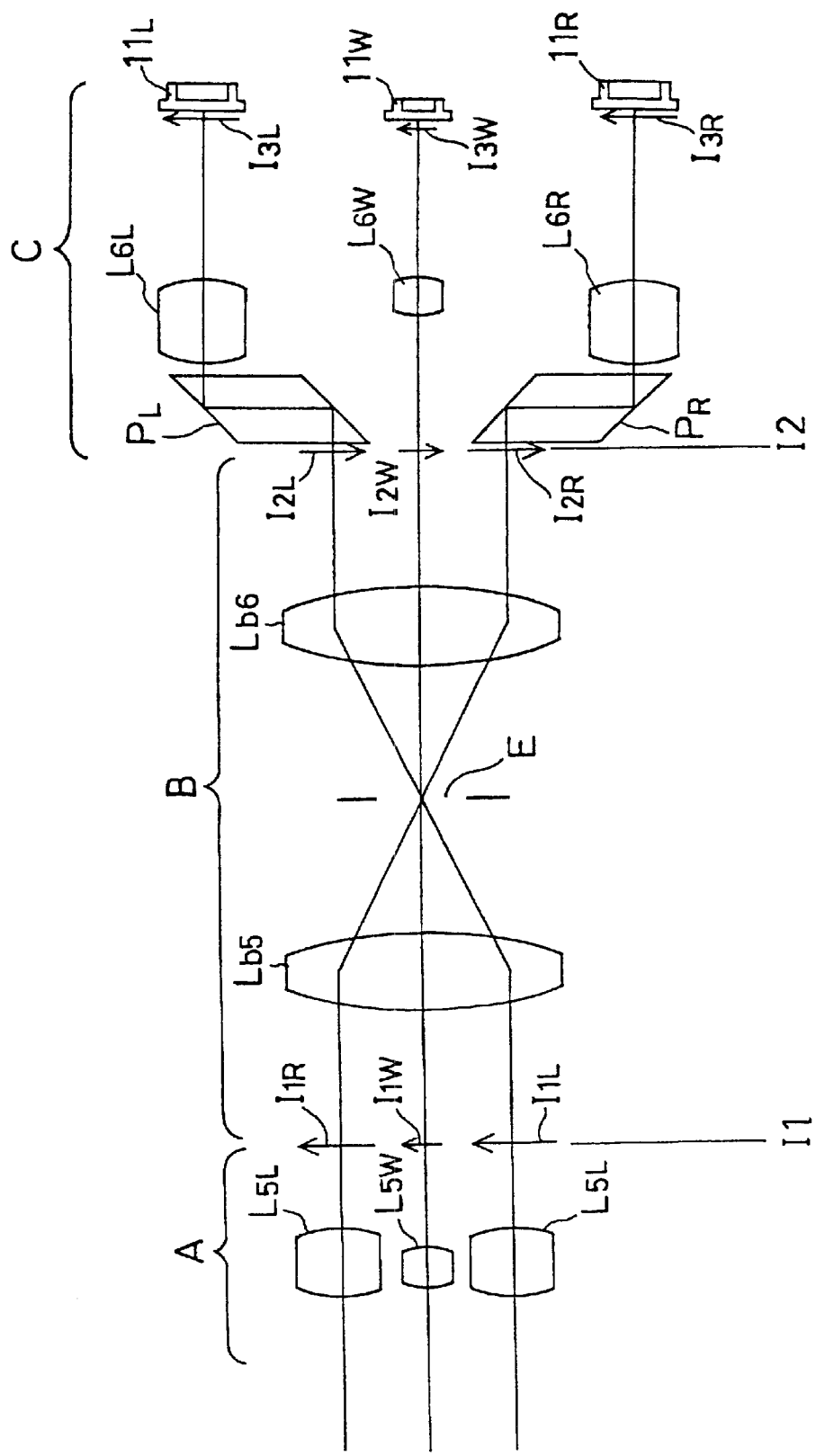
FIG. 4 is an optical-path diagram showing a stereoscopic rigid endoscope optical system according to the second embodiment of the present invention

FIG. 4 is an optical-path diagram showing a stereoscopic rigid endoscope optical system it according to the second embodiment. The stereoscopic rigid endoscope optical system includes objective optical system part A, relay optical system part B, and image-formation optical system part C.

The objective optical system part A is equipped with the primary objective optical system for stereoscopic observation and secondary objective lens system. The primary objective optical system for stereoscopic observation consists of L5L and L5R. The secondary objective optical system consists of L5W. The lens systems L5L and L5R have the same optical property and have comparatively narrow field of view. And the secondary objective lens system L5W has a wider field of view than the primary objective optical system for stereoscopic observation. The lens systems, L5L, L5R, and L5W, have certain angles around the central axis O like shown in FIG. 2(a), and are arranged so that they may have an parallel optical axis. However, FIG. 4 illustrates these three objective lens systems L5L, L5R, and L5W on the same plane in order to make explanation easy. Also in this case, it is desirable that the lens systems L5L and L5R for stereoscopic observation are arranged in the position with an identical distance from the central axis.

The objective lens systems L5L and L5R for stereoscopic observation have narrow fields of view and form images with high resolution. The objective lens system L5W has a wide field of view and is used for finding an organ. For this reason, the aperture diameter of the primary objective lens system L5L and L5R for stereoscopic observation is comparatively large. On the one hand, the aperture diameter of secondary objective lens system L5W is smaller than L5L and L5R. Images I1L, I1R, and I1W made by objective lens systems L5L, L5R, and L5W are formed on the same image plane I1.

These objective optical systems L5L, L5R, and L5W are arranged in parallel and are designed so that their images may not be overlapped on the same image plane I1.

In the relay optical system part B, a pair of lens systems Lb5 and Lb6 is arranged.

The image plane I1 of the objective optical system part A exists at the front focal plane of the first lens system Lb5. The image plane I1 becomes a object plane of the relay optical system part B. The second image plane I2 which conjugates to the image plane I1 is formed at the rear focal plane of the 2nd lens system Lb6. And the front focal plane of Lb6 is arranged at the rear focal plane of Lb5.

On the second image plane I2, the objective optical system images I1L and I1R respectively conjugate the second images I2L and I2R. And the image I2W which conjugates to the secondary objective optical system image I1W is formed similarly apart. Moreover, all the pupils in the relay optical systems are formed in piles on the pupil plane E which is on the rear focal plane of the lens system Lb5.

The relay optical system part B consists of only a cycle of lens system Lb5 and Lb6 in FIG. 4. However, the relay optical system part B may consist of two or more cycles of the lens system Lb5 and Lb6 to make the insertion length longer.

Image-formation optical system part C branches ray bundles from the images I2L, I2R, and I2W. In addition, the optical system part C forms final images I3L, I3R, and I3W on the image-pick-up elements (for example, CCD) 11L, 11R and 11W on either side with image-formation lens systems L6L, L6R and L6W.

The parallelogram prisms PL and PR may respectively be arranged near the images I2L and I2R on either side. PL is arranged to transfer only the ray bundle from the image I2L and PR It is arranged to transfer only the ray bundle from the image I2R. The parallelogram prisms PL and PR shift optical axes respectively in the outside direction in parallel. And the final images I3L and I3R are formed respectively on image-pick-up element 11L and 11R by the right and left image-formation lens systems L3L and L3R of the same optical property.

In this embodiment, the optical path to get the wide angle image I3W is not shifted. And the wide angle image I3W is formed on the image-pick-up element 11W by the image-formation lens system L6W. The prisms PL and PR are partially chipped so that the ray bundle from the pupil I2W may not be rejected by the prisms.

Also in this embodiment, the direction conversion prism unit 12 shown in FIG. 3 can be applicable to obtain the same oblique direction of view.

Next, a example of the specification of the rigid endoscope optical system of the constitution in FIG. 1 is shown.

Effective length of insertion part: 330 mm

Outer diameter of Insertion part: 12 mm

<L1L and L1R>

Lens outer diameter: 4.15 mm

Field of view: 40 degrees

Image height: 1.5 mm

Focal length: 4.46 mm

F-number: 5.8

Best working distance: 35 mm

Distance between axes of L1L and L1R (stereo base length): 4.75 mm

Total length (from the first surface to the image plane): 58.7 mm

<L2L and L2R>

Lens outer diameter: 4.15 mm

Object height: 1.5 mm

Object side NA: 0.086

Total length (from the image plane to the pupil plane): 36.3 mm

<L1W>

Lens outer diameter: 1.9 mm

Field of view: 80 degrees

Image height: 0.64 mm

Focal length: 1.16 mm

F-number: 11.3

Best working distance: 35 mm

Total length (from the first surface to the image plane): 55 mm

<L2W>

Lens outer diameter: 1.9 mm

Object height: 0.64 mm

Object Side NA: 0.044

Total length (from the image plane to the pupil plane): 40 mm

<Relay optical system part B>

Lens outer diameter: 9.5 mm

Number of relay cycles: 2 cycles (1 cycle in FIG. 1)

Relay Length/cycles: 146 mm

Total length (from pupil up to pupil): 292 mm
Maximum image height: 3.7 mm
Maximum NA: 0.1
The Focal-length of Lb1 and Lb2: 45 mm As mentioned above, the rigid endoscope optical system of this invention has been demonstrated based on these embodiments. However, this invention is not limited to these embodiments and other variations are applicable.

The above explanation shows that the rigid endoscope optical system of this invention has the primary narrow angle and the secondary wide angle objective optical systems, and one relay optical system which transmits the images made by the objective optical systems. Therefore, the rigid endoscope optical system can obtain simultaneously the wide angle image for finding an organ and the high resolution image used for the precise treatment. Moreover, since one common relay optical system is used, image quality deterioration is small and the reduction of the number of lens can be performed. Total cost of the system can be reduced. Moreover, the rigid endoscope optical system with both the primary stereoscopic vision and the secondary wide vision is realizable.

What is claimed is:

1. A rigid endoscope optical system comprising:
a primary objective optical system for stereoscopic observation which includes right and left objective optical systems and forms right and left exit pupils on an exit pupil plane at a finite position;
a secondary objective optical system which has a wider field of view and smaller lens diameter than said primary objective optical system and forms an exit pupil on nearly the same plane as the exit pupils of the primary objective optical system;
a relay optical system which transmits said pupils made by said primary objective optical system and said secondary objective optical system and forms exit pupils of said relay optical system on a plane at a finite position; and
an optical means for separating ray bundles which pass through said exit pupils made by said relay optical system.

2. A rigid endoscope optical system comprising:
a primary objective optical system for stereoscopic observation which includes right and left objective optical systems and forms right and left images on an image plane at a finite position;
a secondary objective optical system which has a wider field of view and smaller lens diameter than said primary objective optical system and forms an image on nearly the same plane as the images of the primary objective optical system;
a relay optical system which transmits said images made by said primary objective optical system and said secondary objective optical system and forms images on a plane at a finite position; and
an optical means for separating ray bundles from said images made by said relay optical system.

3. A rigid endoscope optical system comprising:
a primary objective optical system for stereoscopic observation which includes right and left objective optical systems and forms right and left exit pupils on an exit pupil plane at a finite position;
a secondary objective optical system which has a wider field of view than said primary objective optical system and forms an exit pupil on nearly the same plane as the exit pupils of the primary objective optical system; and
a relay optical system which transmits said pupils made by said primary objective optical system and said secondary objective optical system and forms exit pupils of said relay optical system on a plane at a finite position.

4. A rigid endoscope optical system comprising:
a primary objective optical system for stereoscopic observation which comprises right and left objective optical systems and forms right and left images on an image plane at a finite position;
a secondary objective optical system which has a wider field of view than said primary objective optical system and forms an image on nearly the same plane as the images of the primary objective optical system; and
a relay optical system which transmits said images made by said primary objective optical system and said secondary objective optical system and forms images on a plane at a finite position.

5. A rigid endoscope optical system comprising:
a primary objective optical system which forms an exit pupil on an exit pupil plane at finite position;
a secondary objective optical system which has a wider field of view and smaller lens diameter than said primary objective optical system and forms an exit pupil on nearly the same plane as the exit pupil of the primary objective optical system;
a relay optical system which transmits said pupils made by said primary objective optical system and said secondary objective optical system and forms exit pupils of said relay optical system on a plane at a finite position; and
an optical means for separating ray bundles which pass through said exit pupils made by said relay optical system.

6. A rigid endoscope optical system comprising:
a primary objective optical system which forms an image on an image plane at a finite position;
a secondary objective optical system which has a wider field of view and smaller lens diameter than said primary objective optical system and forms an image on nearly the same plane as the image of the primary objective optical system;
a relay optical system which transmits said images made by said primary objective optical system and said secondary objective optical system and forms images of said relay optical system on a plane at a finite a position; and
an optical means for separating ray bundles which pass through said exit pupils made by said relay optical system.

7. A rigid endoscope optical system comprising:
a primary objective optical system which forms an exit pupil on an exit pupil plane at finite positions;
a secondary objective optical system which has a wider field of view than said primary objective optical system and forms an exit pupil on the nearly same plane as the exit pupil of the primary objective optical system; and
a relay optical system which transmits said pupils made by said primary objective optical system and said secondary objective optical system and forms exit pupils of said relay optical system on a plane at a finite position.

8. A rigid endoscope optical system comprising:
a primary objective optical system which forms an image on an image plane at a finite position;

a secondary objective optical system which has a wider field of view than said primary objective optical system and forms an image on nearly the same plane as the image of the primary objective optical system; and a relay optical system which transmits said images made by said primary objective optical system and said secondary objective optical system and forms images of said relay optical system on a plane at a finite position.

9. The rigid endoscope optical system of any one of preceding claims 1 through 8 wherein said primary objective optical system and said secondary objective optical system have the same oblique direction of view, and both said primary objective optical system and said secondary objective optical system share a prism unit to get oblique direction of view.

10. A rigid endoscope optical system comprising:

a right objective optical system which forms a right exit pupil on a plane at a finite position and has a right intermediate image;

a left objective optical system which forms a left exit pupil on the same plane as the right exit pupil and has a left intermediate image;

a relay optical system which transmits said pupils made by said right and left objective optical systems and forms exit pupils of said relay optical system on a plane at a finite position; and an optical means for separating ray bundles which pass through said exit pupils made by said relay optical system.

11. The rigid endoscope optical system of claim 1, 3, 5, or 7 wherein said all the objective optical systems respectively have an intermediate image.

12. The rigid endoscope optical system of claim 1, 3, 5, or 7 wherein said all the exit pupils made by said all the objective optical systems do not overlap respectively on said exit pupil plane.

13. The rigid endoscope optical system of claim 2, 4, 6, or 8 wherein said all the images made by said all the objective optical systems do not overlap respectively on said image plane.

14. A relay optical system for rigid endoscope wherein both an object position and an image position for said relay optical system are designed to be nearly infinite, and both an entrance pupil position and an exit pupil position are finite, and said relay optical system has at least an intermediate real image.

\* \* \* \* \*